(12) United States Patent
Monclin et al.

(10) Patent No.: US 9,902,982 B2
(45) Date of Patent: Feb. 27, 2018

(54) CONTINUOUS COUNTERCURRENT ENZYMATIC HYDROLYSIS OF PRETREATED BIOMASS AT HIGH SOLIDS CONCENTRATIONS

(71) Applicant: API Intellectual Property Holdings, LLC, Atlanta, GA (US)

(72) Inventors: Jean-Pierre Monclin, Atlanta, GA (US); Vesa Pylkkanen, Atlanta, GA (US); Cosmas Bayuadri, Sugar Hill, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

(21) Appl. No.: 14/838,339

(22) Filed: Aug. 27, 2015

(65) Prior Publication Data

US 2016/0060667 A1    Mar. 3, 2016

Related U.S. Application Data

(60) Provisional application No. 62/045,293, filed on Sep. 3, 2014, provisional application No. 62/045,325, filed on Sep. 3, 2014, provisional application No. 62/045,366, filed on Sep. 3, 2014.

(51) Int. Cl.
  *C12P 19/14* (2006.01)
  *C12P 19/02* (2006.01)
(52) U.S. Cl.
  CPC .............. *C12P 19/14* (2013.01); *C12P 19/02* (2013.01); *C12P 2201/00* (2013.01)

(58) Field of Classification Search
  CPC ........ C12P 2201/00; C12P 19/14; C12P 19/02
  See application file for complete search history.

(56) References Cited

FOREIGN PATENT DOCUMENTS

WO    WO 2014019589 A1 *   2/2014   .............. C12P 19/02

OTHER PUBLICATIONS

Kim et al. "Continuous Countercurrent Extraction of Hemicellulose from Pretreated Wood Residues" (2001) Applied Biochemistry and Biotechnology, vol. 91-93: 253-267.*

* cited by examiner

*Primary Examiner* — Robert Yamasaki
*Assistant Examiner* — Teresa E Knight
(74) *Attorney, Agent, or Firm* — O'Connor & Company; Ryan P. O'Connor (57) ABSTRACT

The invention provides a continuous process for enzymatic hydrolysis of pretreated biomass, the process comprising: providing a pretreated lignocellulosic biomass feed material containing cellulose; introducing the pretreated lignocellulosic biomass feed material to a mechanical-treatment unit containing one or more decompression regions configured to release pressure; introducing a liquid solution containing cellulase enzymes to one or more decompression regions in the mechanical-treatment unit, wherein the liquid solution enters void spaces between fibers of the pretreated lignocellulosic biomass feed material, to form enzyme-containing cellulose-rich solids; and retaining the enzyme-containing cellulose-rich solids under effective hydrolysis conditions to hydrolyze at least some of the cellulose to glucose. Various apparatus configurations are disclosed for the mechanical-treatment unit.

15 Claims, 2 Drawing Sheets

FIG. 1

FIG. 2

CONTINUOUS COUNTERCURRENT ENZYMATIC HYDROLYSIS OF PRETREATED BIOMASS AT HIGH SOLIDS CONCENTRATIONS

PRIORITY DATA

This patent application is a non-provisional application claiming priority to U.S. Provisional Patent App. Nos. 62/045,293, 62/045,325, and 62/045,366, each filed Sep. 3, 2014, and each of which is hereby incorporated by reference herein.

FIELD OF THE INVENTION

The present invention generally relates to processes for preparing fermentable sugars from lignocellulosic biomass.

BACKGROUND OF THE INVENTION

Public and private sectors have interest in renewable fuels and chemicals from biomass to replace fossil fuel from finite oil reserves. Woody and herbaceous biomasses are making a comeback after over a century of domination by coal, oil, and natural gas. This interest is driven in part by the carbon-neutral footprint of the biomass. One of the proposed routes is to convert cellulose and hemicellulose to fermentable sugars as a feedstock for bio-based chemicals.

The Green Power+® technology has been developed by American Process, Inc. This technology extracts hemicelluloses from a biomass feedstock supply and converts only those hemicelluloses into sugars which are then fermented, such as to cellulosic ethanol. Green Power+ technology is a two-step process to produce sugars from hemicelluloses. An initial steam or hot-water extraction pulls out hemicelluloses, and the remainder of the biomass is suitable for combustion in a boiler or for pelletization, or for cellulose hydrolysis, or other uses. The extracted solution is then hydrolyzed with a mild acid or enzyme treatment to hydrolyze oligomers into fermentable monomers.

All biomass is composed of cellulose fibers which are bound to hemicelluloses and glued together by lignin to form a matrix, which is naturally deconstruction-resistant. Only after loss of viability, the biomass starts to rot by fungi, which secrete enzymes to deconstruct the biomass matrix. These enzymes are categorized as cellulases, hemicellulases, or laccases depending of targeted function. Recently, these enzymes are harvested for commercial use. The drawbacks of enzymes include slow activity and sensitivity to environmental conditions. This typically leads to long retention times at moderate temperatures, which increases the risk of contamination by bacteria or wild yeast.

The retention time and enzyme dosage can be reduced, if the structural matrix accessibility is improved. The possible pretreatment methods include mechanical, thermal, and chemical methods. In particular, hydrothermal methods can be beneficial for hemicellulose removal. Most of the hemicellulose is soluble in hot pressurized water or steam. After sufficient pretreatment, the cellulose fibers are released from the matrix or can be physically blown apart by a pressure release. This deconstruction allows enzymes an access to the cellulose.

The access requires also a means of introducing the enzyme so that it is effectively distributed into the biomass. This may be difficult, when the amount of enzyme solution is small compared to biomass. Dilute solution facilitates the enzyme transfer into the fibrous material. Low-consistency solutions of up to 8% allow carrier fluid, usually water, to surround fibers in the liquid. Pumping and mixing at this concentration present little challenge. However, the volume of over 90% water makes saccharification process equipment large, and dilutes the subsequent sugar concentration.

Higher temperature can be attempted for faster kinetics and thus smaller equipment. Cellulases and hemicellulases generally have activity at temperatures from 30° C. to 70° C. At the high end of the temperature range, however, the enzyme denatures for permanent loss of activity.

Generally, enzymatic hydrolysis for pretreated biomass requires optimization of enzyme feed as one of the most expensive process components. Some methods use enzyme recycle in a batch mode by squeezing out the enzymes and introducing to fresh biomass, which requires energy and wastes enzyme activity when enzymes bind with high concentrations of non-cellulose fiber active sites (such as lignin). Batch recycling only works for some enzymes that can bind to active sites quickly before being squeezed or removed.

Enzymatic hydrolysis of pretreated biomass remains as a significant commercial challenge for the biorefinery industry. Improved methods of using enzymes, and process and systems incorporating such methods for enzymatic hydrolysis, are desired.

SUMMARY OF THE INVENTION

The present invention addresses the aforementioned needs in the art.

In some variations, the invention provides a continuous process for enzymatic hydrolysis of pretreated biomass, the process comprising:

(a) providing a pretreated lignocellulosic biomass feed material containing cellulose;

(b) introducing the pretreated lignocellulosic biomass feed material to a mechanical-treatment unit containing one or more decompression regions configured to release pressure;

(c) introducing a liquid solution containing cellulase enzymes to the one or more decompression regions in the mechanical-treatment unit, wherein the liquid solution enters void spaces between fibers of the pretreated lignocellulosic biomass feed material, to form enzyme-containing cellulose-rich solids; and (d) retaining the enzyme-containing cellulose-rich solids under effective hydrolysis conditions to hydrolyze at least some of the cellulose to glucose.

In some embodiments, the enzyme-containing cellulose-rich solids have a solids concentration of about 10 wt. % of greater, such as about 20 wt. % or greater.

The pretreated lignocellulosic biomass feed material may be a hydrothermally or thermomechanically treated biomass material. For example, lignocellulosic biomass feed material may be treated with steam and/or hot water and optionally an acid, and with mechanical refining.

The pretreated lignocellulosic biomass feed material may be a chemically treated biomass material. For example, lignocellulosic biomass feed material may be treated with an acid catalyst, a solvent for lignin, and water.

In some embodiments, the process further comprises recovering hydrolyzed hemicelluloses derived from the lignocellulosic biomass, wherein the hydrolyzed hemicelluloses are obtained separately from step (d) or in step (d). In certain embodiments, the process further comprises recycling sugar oligomers obtained during step (d) back to step (c). When the liquid solution contains hemicellulose enzymes, the process may include recovering the hydrolyzed hemicelluloses in step (d) or following step (d). Optionally, the hydrolyzed hemicelluloses may be combined with the glucose, to generate a combined sugar stream.

The mechanical-treatment unit may be operated countercurrently, i.e., so that the liquid solution and the pretreated lignocellulosic biomass feed material are in countercurrent flow. In some embodiments, the mechanical-treatment unit is or includes a ribbon screw conveyor with reverse pitch screw. In some embodiments, the mechanical-treatment unit is or includes a countercurrent screw with perforated blades that allow liquid to flow in different directions. In certain embodiments, the mechanical-treatment unit is or includes a countercurrent system comprising two cross-flow reactors connected by a transfer screw. The mechanical-treatment unit may include a single-shaft conveyor, a ribbon in an entry side, and a distal screw with reverse pitch, preferably wherein the screw has a smaller diameter than the internal diameter of the ribbon.

In some embodiments, step (d) is conducted in the mechanical-treatment unit. Alternatively, or additionally, step (d) is conducted in a separate reactor or chamber configured to mechanically mix the enzyme-containing cellulose-rich solids.

DETAILED DESCRIPTION OF EMBODIMENTS OF THE INVENTION

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Variations of this invention relate, in general, to the preparation of biomass and application of cellulase and hemicellulase at high consistency (solids content). Particular apparatus are disclosed to perform enzymatic liquefaction and saccharification. The present inventors have developed an effective method to introduce enzymes in the biomass after pretreatment and an apparatus to perform partial liquefaction and saccharification, while resulting in high concentration of the released sugars. The pretreatment method may be hydrothermal, with or without acid catalyst, or another pretreatment method.

Variations of the invention are premised on the principle of introducing enzyme solution at one or more critical points, where there is decompression of biomass which allows an even distribution of the liquid and deeper liquid (containing enzymes) penetration into the solid. Some embodiments utilize biomass compression and enzyme addition at a decompression point, resulting in biomass liquefaction at high consistency.

Figure 1:
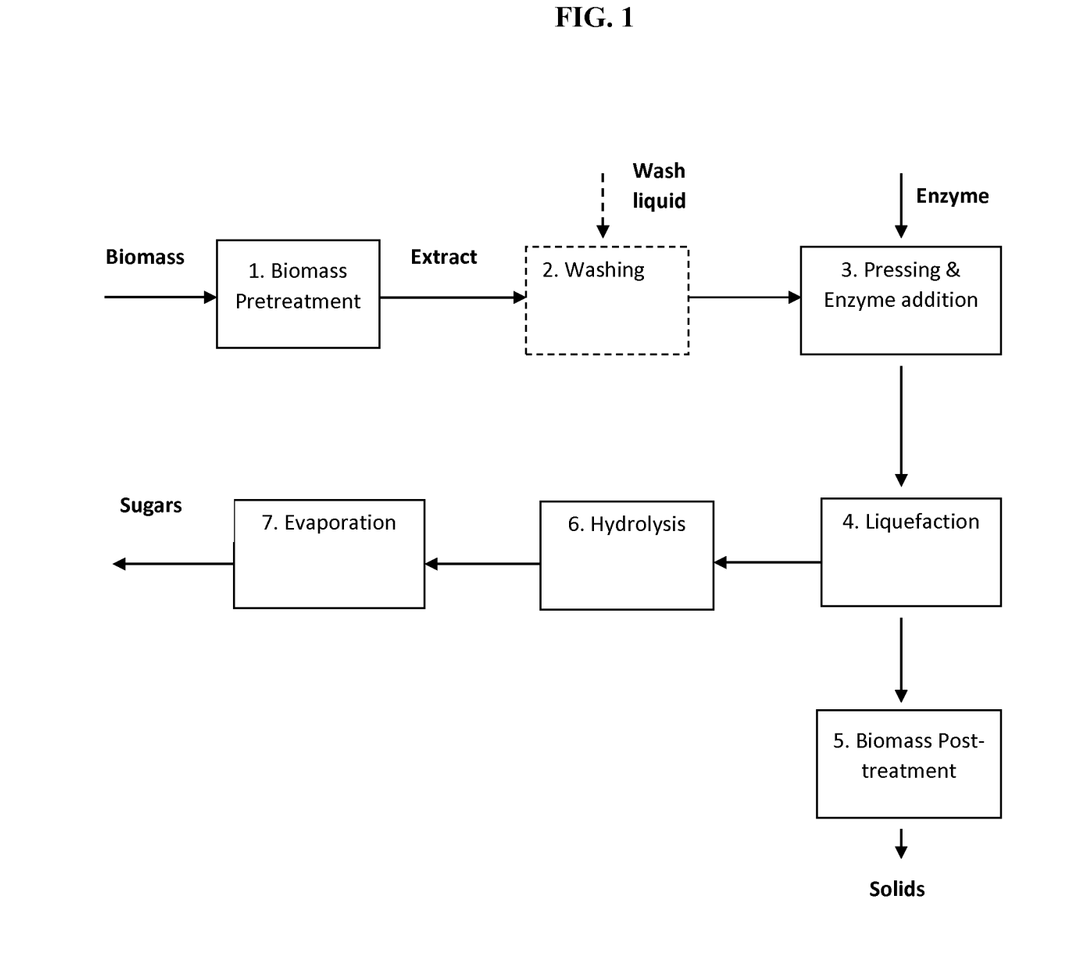
FIG. 1 is a simplified block-flow diagram depicting the process of some embodiments of the present invention.

FIG. 1 illustrates an exemplary flow diagram of a high-consistency enzymatic application process, noting that the process steps may be in other sequences. This stepwise processing of biomass produces solids and sugar solution. It is understood the steps may be omitted or practiced in a different order within the scope of the invention. The following reference to steps are in reference to some embodiments only.

The first step of the process is the pretreatment of the biomass. The biomass is cut or ground to reduce uniform particle size. Then biomass is fed to a pressurized vessel operating either continuously or in batch mode. The particles are digested in aqueous solution in temperature of approximately between 100° C. and 250° C., for example 150° C., 16° C., 170° C., 180° C., 190° C., 200° C. or 210° C. (most preferably 180° C. to 210° C.). The liquor may contain acidifying compound such as sulfuric acid, sulfurous acid, sulfur dioxide, acetic acid, formic acid, oxalic acid, or a combination thereof. The dilute acid concentration can range from 0.01 wt % to 10 wt % as necessary to improve hemicelluloses solubility, or for other reasons. The vessel is depressurized upon exit of the vessel to form fibrous pulp.

The second step consists of washing the extracted biomass fibers. The washing may be accomplished with water, recycled condensates or permeate, or a combination thereof.

A countercurrent configuration may be used to maximize the extract concentration. Washing removes most of the dissolved material, including hemicelluloses. The final consistency of the washing is increased to about 20 wt % or more, preferably to 30 wt % or more, using any mechanical pressing device, such as a wash press, a screw press, a filter press, or a rotating vacuum drum filter.

The third step uses a mechanical pressing device that has one or more stages wherein the pressure is released or reduced. Pressure reduction may be accomplished by vacuum, removal of gases or liquids through a valve, adjustment of mechanical forces within the apparatus (e.g., via screw design), or by other means. Enzyme solution may be introduced (such as from an external tank and into the device) at one or more of these decompression points. There may be 1, 2, 3, 4, 5 or more decompression points or zones. Without being limited by theory, upon decompression of the fiber, the solution of enzymes fills the void space between fibers and, by an adsorption-diffusion mechanism, reaches the matrix structure of the fiber.

The fourth step consists of retention of the pressed material to partial liquefaction and saccharification. This may be accomplished in a chamber with mixing of high-consistency fiber. The mixing may be performed using a screw conveyer, for example. A countercurrent double helix, in some embodiments, aids mixing of the high-consistency fiber. Liquefied oligomer solution can be recycled, at least in part, back to the third step. In another manifestation, a rotary drum is used for mixing. In yet another manifestation, a static drum with mechanized mixing is employed. Other devices include high-shear-rate mixing devices (e.g., ribbon screw conveyor with reverse pitch screw, paddle mixing conveyor, disc refiner, grinder with hammer or knives, etc.).

The fifth step is post-treatment of the residual biomass. This process may include grinding, milling, fluidizing, or pelletizing of the residual biomass (solids following extraction) to generate fine powder, loose fiber, pellets, or briquettes, for example.

The sixth step is the optional hydrolysis of the biomass extract. The extract may be hydrolyzed using dilute acid (e.g., mineral acid or organic acid) at temperatures between 90° C. and 190° C., for example 100° C., 110° C., 120° C., 130° C., 140° C. or 150° C. and most preferably from 100° C. to 120° C. A mineral acid may include sulfuric acid, sulfurous acid, phosphoric acid, nitric acid, or sulfur dioxide. An organic acid may include formic acid, acetic acid, or oxalic acid from the cooking liquor or recycled back from the hydrolysis step. Alternatively, hemicellulase enzymes may be used instead of acids for hydrolysis. The lignin from this step may be separated and returned to the fourth step with the solid product.

The seventh step is evaporation or steam stripping, or a combination of both, of the hydrolyzate to remove some or most of the volatile organic acids. The evaporation may include a flashing step or cooling step beforehand to remove sulfur dioxide or other acids. The evaporation step may be performed below the acetic acid dissociation pH of 4.8 and most preferably between pH 1 and 2.5, in some embodiments. Some or all the organic acid-containing condensate may be used for the cooking step and/or washing step. The dissolved solids may concentrated from to about 10 wt %, 20 wt %, 30 wt %, or higher, consisting mostly of fermentable hemicellulose sugars.

This hemicellulosic sugar solution may be fermented to produce biochemicals and/or biofuels. The products may include ethanol, butanol, acetic acid, lactic acid, succinic acid, or other fermentation products. Any leftover lignocellulosic material from the bottoms of distillation can be concentrated and added to the solids in the step four.

Some variations of the invention pertain to methods, systems, and apparatus for enzymatic hydrolysis of biomass and pretreated biomass in the form of cellulose fibers.

In some embodiments, the hydrolysis apparatus consists of a counterflow enzyme ribbon mixer with reverse pitch. For example, an apparatus may include a single-shaft conveyor with ribbon in the entry side and screw with reverse pitch at the other extremity. The screw diameter is preferably smaller diameter than the ribbon internal diameter. This configuration allows mixing of cellulose fiber and enzymes. At the end of the conveyor, there may be a screen for the separation of liquid rich in sugar oligomers, while the remaining cellulose-rich fiber is sent to the next process step(s).

In some embodiments, a continuous countercurrent hydrolysis reactor is used which recognizes that low-activity enzymes are contacted with fresh biomass, binding with non-fiber active sites. The higher-activity enzymes are contacted with pretreated biomass with a high concentration of available active sites are on the fiber to be attacked. As the fiber dissolves and breaks down, the high strength of enzyme attacks the fine fibers with a high hydrolysis reaction rate.

Such displacement of solids with countercurrent enzyme flow can be done in a screw-type reactor, optionally with perforated blades that allows liquid to flow in different directions. The gaps from the blade to the wall, the blade style, and distance between blades are adjusted to minimize the possibility of compaction of biomass against the wall or between blades, allowing a steady push of biomass in one direction. This way, the enzymes can flow steadily through the fiber and the probability of contact between enzymes and active sites increases continuously regardless of the enzyme dosage.

In a single vertical vessel with screw in the middle, countercurrent biomass vs. enzyme feed, the undissolved solids will pose a problem if accumulated on the bottom. In such a configuration, fresh enzyme can also be wasted through the lignin solids outlet.

Figure 2:
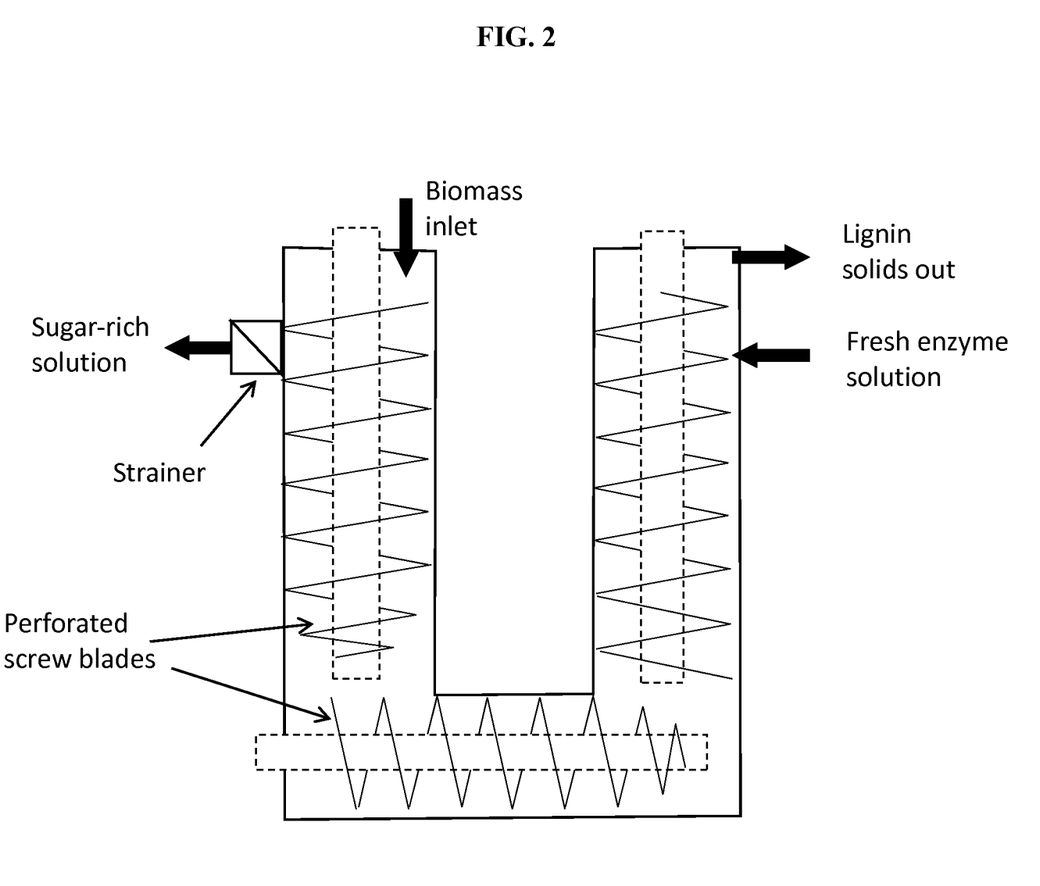
FIG. 2 is a sketch of an apparatus for enzymatic hydrolysis of pretreated biomass, according to certain embodiments of the invention.

One solution is to invert the flow on the second section of the screw reactor so the unreacted solids can be pushed up against gravity and discarded. In this region, enzymes are at their highest activity and fibers are at their smallest size, making it less dependent to the direction of flow or turbulence due to gravity and feed inlet. FIG. 2 is an example of such a continuous countercurrent enzymatic hydrolysis reactor. Two cross-flow reactors are connected by a short horizontal screw to transfer material, while maintaining a countercurrent flow pattern.

This configuration (FIG. 2) can avoid wasting high-activity enzymes on high-lignin, dirty biomass. Other benefits may include:
1. Easy optimization on enzyme dosage and retention time by adjusting screw speed.
2. Fully developed gradient of concentration and enzyme activity control.
3. Energy savings.
4. Flexibility on solids consistency.
5. No pressing or squeezing required (optionally, a decompression region may be included).
6. Low sugar loss with solids effluent.
7. Low enzyme loss carried by solids effluent.

In some variations, the invention provides a continuous process for enzymatic hydrolysis of pretreated biomass, the process comprising:

(a) providing a pretreated lignocellulosic biomass feed material containing cellulose;

(b) introducing the pretreated lignocellulosic biomass feed material to a mechanical-treatment unit containing one or more decompression regions configured to release pressure;

(c) introducing a liquid solution containing cellulase enzymes to the one or more decompression regions in the mechanical-treatment unit, wherein the liquid solution enters void spaces between fibers of the pretreated lignocellulosic biomass feed material, to form enzyme-containing cellulose-rich solids; and (d) retaining the enzyme-containing cellulose-rich solids under effective hydrolysis conditions to hydrolyze at least some of the cellulose to glucose.

In some embodiments, the enzyme-containing cellulose-rich solids have a solids concentration of about 10 wt % of greater, such as about 15 wt %, 20 wt %, 25 wt %, 30 wt % or greater.

The pretreated lignocellulosic biomass feed material may be a hydrothermally or thermomechanically treated biomass material. For example, lignocellulosic biomass feed material may be treated with steam and/or hot water and optionally an acid, and with mechanical refining.

The pretreated lignocellulosic biomass feed material may be a chemically treated biomass material. For example, lignocellulosic biomass feed material may be treated with an acid catalyst, a solvent for lignin, and water.

In various embodiments, the pretreated lignocellulosic biomass feed material is produced by a process or system described in one or more of the following patents: U.S. Pat. Nos. 8,030,039 (Oct. 4, 2011); U.S. Pat. No. 8,038,842 (Oct. 11, 2011); U.S. Pat. No. 8,268,125 (Sep. 18, 2012); U.S. Pat. No. 8,585,863 (Nov. 19, 2013); U.S. Pat. No. 8,864,941 (Oct. 21, 2014); U.S. Pat. No. 9,012,188 (Apr. 21, 2015); U.S. Pat. No. 8,211,680 (Jul. 3, 2012); U.S. Pat. No. 8,518,672 (Aug. 27, 2013); U.S. Pat. No. 8,518,213 (Aug. 27, 2013); U.S. Pat. No. 8,679,364 (Mar. 25, 2014); U.S. Pat. No. 8,845,923 (Sep. 30, 2014); U.S. Pat. No. 8,685,685 (Apr. 1, 2014); U.S. Pat. No. 9,085,494 (Jul. 21, 2015); U.S. Pat. No. 8,785,155 (Jul. 22, 2014); U.S. Pat. No. 8,906,657 (Dec. 9, 2014); U.S. Pat. No. 8,685,167 (Apr. 1, 2014); and/or U.S. patent application Ser. No. 13/626,220 filed Sep. 25, 2012, each of which is hereby incorporated by reference herein.

In some embodiments, the process further comprises recovering hydrolyzed hemicelluloses derived from the lignocellulosic biomass, wherein the hydrolyzed hemicelluloses are obtained separately from step (d) or in step (d). In certain embodiments, the process further comprises recycling sugar oligomers obtained during step (d) back to step (c). When the liquid solution contains hemicellulose enzymes, the process may include recovering the hydrolyzed hemicelluloses in step (d) or following step (d). Optionally, the hydrolyzed hemicelluloses may be combined with the glucose, to generate a combined sugar stream.

The mechanical-treatment unit may be operated countercurrently, i.e., so that the liquid solution and the pretreated lignocellulosic biomass feed material are in countercurrent flow. In some embodiments, the mechanical-treatment unit is or includes a ribbon screw conveyor with reverse pitch screw. In some embodiments, the mechanical-treatment unit is or includes a countercurrent screw with perforated blades that allow liquid to flow in different directions. In certain embodiments, the mechanical-treatment unit is or includes a countercurrent system comprising two cross-flow reactors connected by a transfer screw. The mechanical-treatment unit may include a single-shaft conveyor, a ribbon in an entry side, and a distal screw with reverse pitch, preferably wherein the screw has a smaller diameter than the internal diameter of the ribbon.

In some embodiments, step (d) is conducted in the mechanical-treatment unit. Alternatively, or additionally, step (d) is conducted in a separate reactor or chamber configured to mechanically mix the enzyme-containing cellulose-rich solids.

Some variations provide a mechanical-treatment unit containing one or more decompression regions configured to release pressure, such that liquid solution contained therein can enter void spaces between cellulose fibers of pretreated lignocellulosic biomass feed material that is passing through the mechanical-treatment unit. The mechanical-treatment unit may have 1, 2, 3, 4, 5, 6, 7, 8, 9, 10 or more decompression regions (where a "region" may be a point, a zone, a transfer pipe, and so on). Pressure reduction in a decompression region may be accomplished by vacuum, removal of gases or liquids through a valve, adjustment of mechanical forces within the apparatus (e.g., via screw design), or by other means. Different decompression regions may release or reduce pressure by different modes of action. The mechanical-treatment unit is also configured with one or more inputs for enzyme solution to be introduced at or near decompression regions. For example, an internal ring may be adapted to spray enzyme solution into the biomass material as it is being decompressed, and/or after it has been decompressed.

In some variations, a process for producing fermentable sugars from cellulosic biomass, comprises:

(a) providing a feedstock comprising cellulosic biomass;

(b) extracting the feedstock with an extraction solution including steam and/or hot water under effective extraction conditions to produce an extract liquor containing hemicellulose oligomers, dissolved lignin, and cellulose-rich solids;

(c) separating at least a portion of the cellulose-rich solids from the extract liquor, to produce washed cellulose-rich solids;

(d) removing a portion of glucan contained in the washed cellulose-rich solids by contacting the washed cellulose-rich solids with a liquefaction-focused blend of enzymes, to release glucose oligomers;

(e) co-hydrolyzing the glucose oligomers and the hemicellulose oligomers, with enzymes or an acid catalyst, to produce glucose and hemicellulose monomers; and (f) recovering the glucose and hemicellulose monomers as fermentable sugars.

In some embodiments, the extraction solution comprises steam in saturated, superheated, or supersaturated form. In some embodiments, the extraction solution comprises hot water. Additives may be present, such as acid or base catalysts, or other compounds present in recycled streams.

In some embodiments, step (c) includes washing the cellulose-rich solids using an aqueous wash solution, to produce a wash filtrate; and optionally combining at least some of the wash filtrate with the extract liquor. In some of these embodiments, step (c) further includes pressing the cellulose-rich solids to produce the washed cellulose-rich solids and a press filtrate; and optionally combining at least some of the press filtrate with the extract liquor.

Step (c) may include countercurrent washing, such as in two, three, four, or more washing stages. Step (d) may be integrated with step (c), and in certain embodiments, step (c) and step (d) are conducted in a single unit. That is, the separation/washing in step (c) may be combined with the application of the liquefaction-focused blend of enzymes in step (d), in various ways.

The application of the liquefaction-focused blend of enzymes may be conducted prior to a first washing stage, during (integrated with) a first washing stage, between a first and second washing stage, during (integrated with) a second washing stage, after a second washing stage, or during (integrated with) or after a later washing stage.

In some embodiments, the liquefaction-focused blend of enzymes in step (d) includes both endoglucanases and exoglucanases. Endoglucanases are cellulases that attack low-crystallinity regions in the cellulose fibers by endoaction, creating free chain-ends; exoglucanases or cellobiohydrolases are cellulases that hydrolyze the 1,4-glycocidyl linkages to form cellobiose.

Other cellulase enzymes may be utilized as recited in Verardi et al., "Hydrolysis of Lignocellulosic Biomass: Current Status of Processes and Technologies and Future Perspectives," *Bioethanol*, Prof Marco Aurelio Pinheiro Lima (Ed.), ISBN: 978-953-51-0008-9, InTech (2012), which is hereby incorporated by reference.

Thermotolerant enzymes may be employed, in various embodiments of the invention. For example, in some embodiments, a suitable enzyme is utilized at high temperature for only hydrolysis and little or no saccharification (i.e., no production of glucose monomer) and then the temperature is decreased after which the enzyme may also accomplish saccharification.

The process may further comprise refining or milling the washed cellulose-rich solids prior to or during step (d).

When step (e) employs enzymes, these enzymes will typically contain cellulases and hemicellulases. The cellulases here may include β-glucosidases that convert cellooligosaccharides and disaccharide cellobiose into glucose. There are a number of enzymes that can attack hemicelluloses, such as glucoronide, acetylesterase, xylanase, β-xylosidase, galactomannase and glucomannase. Exemplary acid catalysts for step (e) include sulfuric acid, sulfur dioxide, hydrochloric acid, phosphoric acid, and nitric acid.

The process further comprises a step of fermenting the fermentable sugars to a fermentation product, in some embodiments.

Other variations provide a process for producing fermentable sugars from cellulosic biomass, the process comprising:

(a) providing a feedstock comprising cellulosic biomass;

(b) extracting the feedstock with steam and/or hot water under effective extraction conditions to produce an extract liquor containing hemicellulose oligomers, dissolved lignin, and cellulose-rich solids;

(c) separating at least a portion of the cellulose-rich solids from the extract liquor, to produce washed cellulose-rich solids;

(d) removing a portion of glucan contained in the washed cellulose-rich solids by contacting the washed cellulose-rich solids with a liquefaction-focused blend of enzymes, to release glucose oligomers;

(e) hydrolyzing the glucose oligomers with a first hydrolysis catalyst, to produce glucose;

(f) hydrolyzing the hemicellulose oligomers with a second hydrolysis catalyst, to produce hemicellulose monomers; and (g) recovering the glucose and hemicellulose monomers, individually or in combination, as fermentable sugars.

In some embodiments, the first hydrolysis catalyst includes cellulases. In some embodiments, the second hydrolysis catalyst includes hemicellulases. In other embodiments, the first hydrolysis catalyst and the second hydrolysis catalyst are acid catalysts. The first hydrolysis catalyst may be the same as, or different than, the second hydrolysis catalyst.

In some embodiments, the glucose is recovered in a separate stream from the hemicellulose monomers. In other embodiments, the glucose and the hemicellulose monomers are recovered in the same stream. The process may include fermentation of the glucose and/or the fermentable hemicellulose sugars to a fermentation product.

The biomass feedstock may be selected from hardwoods, softwoods, forest residues, agricultural residues (such as sugarcane bagasse), industrial wastes, consumer wastes, or combinations thereof. In any of these processes, the feedstock may include sucrose. When the starting biomass material contains sucrose, it may be present in a concentration of (for example) from about 0.5 wt % to about 10 wt % sucrose, or from about 1 wt % to about 5 wt % sucrose. In some embodiments with sucrose present in the feedstock, a majority of the sucrose is recovered as part of the fermentable sugars. In order to preserve sucrose, it is preferred to utilize enzymes rather than acid catalysts for cellulose hydrolysis.

In some embodiments, the process starts as biomass is received or reduced to approximately ¼" thickness. In a first step of the process, the biomass chips are fed to a pressurized extraction vessel operating continuously or in batch mode. The chips may be steamed or water-washed to remove dirt and entrained air. The chips are immersed with aqueous liquor or saturated vapor and heated to a temperature between about 100° C. to about 250° C., for example 150° C., 160° C., 170° C., 180° C., 190° C., 200° C., or 210° C. Preferably, the chips are heated to about 180° C. to 210° C. The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration can range from 0.01% to 10% as necessary to improve solubility of particular minerals, such as potassium, sodium, or silica. Preferably, the acid concentration is selected from about 0.01% to 4%, such as 0.1%, 0.5%, 1%, 1.5%, 2%, 2.5%, 3%, or 3.5%.

A second step may include depressurization of the extracted chips. The vapor can be used for heating the incoming woodchips or cooking liquor, directly or indirectly. The volatilized organic acids (e.g., acetic acid), which are generated or included in the cooking step, may be recycled back to the cooking.

A third step may include washing the extracted chips. The washing may be accomplished with water, recycled condensates, recycled permeate, or combination thereof. A liquid biomass extract is produced. A countercurrent configuration may be used to maximize the biomass extract concentration. Washing typically removes most of the dissolved material, including hemicelluloses and minerals. The final consistency of the dewatered cellulose-rich solids may be increased to 30% or more, preferably to 50% or more, using a mechanical pressing device.

The third step, or an additional step prior to drying, may include further hydrolyzing the extracted chips with a liquefaction-focused blend of enzymes to convert some of the cellulose to glucose oligomers. In some preferred embodiments, the additional hydrolysis is mild hydrolysis that leaves a substantial portion of cellulose in the extracted solids. The mild hydrolysis can take advantage of the initial extraction (first step) of most or all of the hemicellulosic material, leaving a somewhat hollow structure. The hollow structure can increase the effectiveness of cellulose hydrolysis, such as by reducing mass-transfer limitations of enzymes or acids in solution.

When enzymes are employed for the cellulose hydrolysis, the enzymes are preferably cellulase enzymes. Enzymes may be introduced to the extracted chips along with the wash solution, e.g. water, recycled condensates, recycled permeate, or combinations thereof. Alternatively, or additionally, enzymatic hydrolysis may be carried out following washing and removal of hemicelluloses, minerals, and other soluble material.

Enzymes may be added to the extracted chips before or after mechanical pressing. That is, enzymatic hydrolysis may be carried out and then the solids pressed to final consistency; or, the solids may be pressed to high consistency (e.g., 30% or more) and then enzymes introduced to carry out cellulose hydrolysis. It may be beneficial to conduct refining or milling of the dewatered cellulose-rich solids prior to the enzymatic hydrolysis.

The enzymatic hydrolysis may be achieved in a separate unit, such as between washing and drying, or as an integrated part of washing. In some embodiments, at least a portion of enzymes are recycled in a batch or continuous process.

Some embodiments of the invention are premised on the use of rotating apparatus so that cellulose-rich solids and enzymes may be combined and mixed at high solids consistency. For example, a unit similar to a cement mixer may be utilized. Optionally, metal balls or another means of mechanical pressing may be included in the rotating unit. Also, the unit may be configured with a screen for continuous liquid removal (the liquid containing hydrolyzed sugars in monomer or oligomer form). The solids consistency may be about 10 wt %, 15 wt %, 20 wt %, 25 wt %, 30 wt %, 35 wt %, 40 wt %, 45 wt %, 50 wt % or higher, for example. The rotation may be performed continuously or periodically.

In certain embodiments, a rotary kiln (such as a lime kiln) is retrofitted to be used for enzymatic hydrolysis.

When an acid is employed for the cellulose hydrolysis, the acid may be selected from sulfuric acid, sulfurous acid, sulfur dioxide, formic acid, acetic acid, oxalic acid, or combinations thereof. Dilute-acid hydrolysis is preferred, to avoid sugar degradation. Acids may be introduced to the extracted chips along with the wash solution, e.g. water, recycled condensates, recycled permeate, or combinations thereof. Alternatively, or additionally, acid hydrolysis may be carried out following washing and removal of hemicelluloses, minerals, and other soluble material.

Acids may be added to the extracted chips before or after mechanical pressing. That is, acid hydrolysis may be carried out and then the solids pressed to final consistency; or, the solids may be pressed to high consistency (e.g., 30% or more) and then acids introduced to carry out cellulose hydrolysis. It may be beneficial to conduct refining or milling of the dewatered cellulose-rich solids prior to the acid hydrolysis.

The acid hydrolysis may be achieved in a separate unit, such as between washing and drying, or as an integrated part of washing. In some embodiments, at least a portion of the acid is recycled in a batch or continuous process.

A fourth step may include drying of the extracted material to a desired final moisture. The heat necessary for drying may be derived from combusting part of the starting biomass. Alternatively, or additionally, the heat for drying may be provided by other means, such as a natural gas boiler or other auxiliary fossil fuel, or from a waste heat source.

A fifth step may include preparing the biomass for combustion. This step may include refining, milling, fluidizing, compacting, and/or pelletizing the dried, extracted biomass. The biomass may be fed to a boiler in the form of fine powder, loose fiber, pellets, briquettes, extrudates, or any other suitable form. Using known equipment, biomass may be extruded through a pressurized chamber to form uniformly sized pellets or briquettes.

A sixth step may include treatment of the biomass extract to form a hydrolysate comprising fermentable hemicellulose sugars. In some embodiments, the biomass extract is hydrolyzed using dilute acidic conditions at temperatures between about 100° C. and 190° C., for example about 120° C., 130° C., 140° C., 150° C., 160° C., or 170° C., and preferably from 120° C. to 150° C.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis. Alternatively, hemicellulase enzymes may be used instead of acid hydrolysis. The lignin from this step may be separated and recovered, or recycled to increase the heating value of the pellets, or sent directly to the boiler.

A seventh step may include evaporation of hydrolysate to remove some or most of the volatile acids. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. The dissolved solids are concentrated, such as to about 10% to about 40% to optimize fermentable hemicellulose sugar concentration to a particular microorganism. *Saccharomyces Cerevisiae* fermentation can withstand dissolved solids concentrations of 30-50%, while *Clostridia Acetobutylicum* fermentation is viable at 10-20% concentrations only, for example.

In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) and/or third step (washing step) to remove assist in the removal of minerals from the biomass. This recycle of organic acids, such as acetic acid, may be optimized along with process conditions that may vary depending on the amount recycled, to improve the cooking and/or washing effectiveness.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse.

In some embodiments, the fermentable hemicellulose sugars are recovered from solution, in purified form. In some embodiments, the fermentable hemicellulose sugars are fermented to produce of biochemicals or biofuels such as (but by no means limited to) ethanol, 1-butanol, isobutanol, acetic acid, lactic acid, or any other fermentation products.

A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning as additional liquefied biomass, after concentration of the distillation bottoms.

Part or all of the residual solids may be co-combusted with the energy-dense biomass, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

Optionally, the process may include co-combusting the recovered lignin with the energy-dense biomass, to produce power. The recovered lignin may be combined with the energy-dense biomass prior to combustion, or they may be co-fired as separate streams. When recovered lignin is combined with the energy-dense biomass for making pellets, the lignin can act as a pellet binder.

Part or all of the residual solids may be co-combusted with the energy-dense biomass, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of the vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A continuous process for enzymatic hydrolysis of a pretreated lignocellulosic biomass feed material containing cellulose, said process comprising:
   (a) providing said pretreated lignocellulosic biomass feed material containing cellulose;
   (b) introducing said pretreated lignocellulosic biomass feed material to a mechanical-treatment unit containing one or more decompression regions configured to release pressure, wherein said mechanical-treatment unit includes a counterflow enzyme ribbon mixer comprising a single-shaft conveyor for feeding the pretreated biomass into the mechanical-treatment unit at a proximal entry side, a ribbon mixer blade in the proximal entry side, and a screw with reverse pitch at a distal side of the mechanical-treatment unit, wherein the counterflow enzyme ribbon mixer configuration enables mixing of the pretreated lignocellulosic biomass and cellulase enzymes;
   (c) introducing a liquid solution containing cellulase enzymes to said one or more decompression regions in said mechanical-treatment unit, wherein cellulose fibers in said lignocellulosic biomass are decompressed at said decompression regions to produce void spaces between said fibers and wherein said liquid solution enters said void spaces to form enzyme-containing cellulose-rich solids; and
   (d) retaining said enzyme-containing cellulose-rich solids under effective hydrolysis conditions to hydrolyze at least some of said cellulose to glucose.

2. The process of claim 1, wherein said enzyme-containing cellulose-rich solids have a solids concentration of about 10 wt % or greater.

3. The process of claim 2, wherein said solids concentration is about 20 wt % or greater.

4. The process of claim 1, wherein said pretreated lignocellulosic biomass feed material is a hydrothermally or thermomechanically treated biomass material.

5. The process of claim 4, wherein said pretreated lignocellulosic biomass feed material is treated with steam and/or hot water and optionally an acid, and with mechanical refining.

6. The process of claim 1, wherein said pretreated lignocellulosic biomass feed material is a chemically treated biomass material.

7. The process of claim 6, wherein said pretreated lignocellulosic biomass feed material is treated with an acid catalyst, a solvent for lignin, and water.

8. The process of claim 1, said process further comprising recycling sugar oligomers obtained during step (d) back to step (c).

9. The process of claim 1, said process further comprising recovering hydrolyzed hemicelluloses derived from said lignocellulosic biomass, wherein said hydrolyzed hemicelluloses are obtained separately from step (d) or in step (d).

10. The process of claim 9, wherein said liquid solution further contains hemicellulose enzymes, and wherein said process comprises recovering said hydrolyzed hemicelluloses in step (d) or following step (d).

11. The process of claim 9, wherein said hydrolyzed hemicelluloses are combined with said glucose, to generate a combined sugar stream.

12. The process of claim 1, wherein said mechanical-treatment unit is operated so that said liquid solution and said pretreated lignocellulosic biomass feed material are in countercurrent flow.

13. The process of claim 1, wherein said mechanical-treatment unit includes a countercurrent screw with perforated blades that allow liquid to flow in different directions.

14. The process of claim 1, wherein said screw has a smaller diameter than the internal diameter of said ribbon.

15. The process of claim 1, wherein step (d) is conducted in said mechanical-treatment unit.

* * * * *